United States Patent
Patel et al.

(10) Patent No.: US 11,464,735 B2
(45) Date of Patent: Oct. 11, 2022

(54) FIXED DOSE ORAL TESTOSTERONE UNDECANOATE COMPOSITIONS AND USE THEREOF

(71) Applicant: Lipocine Inc., Salt Lake City, UT (US)

(72) Inventors: Mahesh V. Patel, Salt Lake City, UT (US); Nachiappan Chidambaram, Sandy, UT (US); Kilyoung Kim, West Jordan, UT (US)

(*) Notice: Subject to any disclaimer, the term of this patent is extended or adjusted under 35 U.S.C. 154(b) by 215 days.

(21) Appl. No.: 17/033,198

(22) Filed: Sep. 25, 2020

(65) Prior Publication Data

US 2021/0007978 A1 Jan. 14, 2021

(51) Int. Cl.
*A61K 31/568* (2006.01)
*A61K 9/00* (2006.01)
*A61P 5/26* (2006.01)
*C07J 1/00* (2006.01)

(52) U.S. Cl.
CPC .......... *A61K 9/0053* (2013.01); *A61K 31/568* (2013.01); *A61P 5/26* (2018.01)

(58) Field of Classification Search
CPC ........ C07J 1/00; A61K 31/568; A61K 9/0053; A61K 9/4858; A61P 5/26
See application file for complete search history.

(56) References Cited

PUBLICATIONS

Yin et al., Reexamination of Pharmacokinetics of Oral Testosterone Undecanoate in Hypogonadal Men With a New Self-Emulsifying Formulation, Journal of Andrology, vol. 12, No. 2, pp. 190-201 (Year: 2012).*

* cited by examiner

*Primary Examiner* — Brenda L Coleman
(74) *Attorney, Agent, or Firm* — Michael R. Schramm

(57) ABSTRACT

Disclosed are effective fixed dose oral testosterone undecanoate compositions for use in regimens without dose titration and methods for treatment of patients in need of testosterone replacement therapy. Also disclosed are criteria for continuation and discontinuation of such regimens, based on single serum T concentration levels measured at a steady state at predetermined times after initiation of said regimen and at a predetermined number of hours after administration of a morning dose of the regimen.

36 Claims, No Drawings

FIXED DOSE ORAL TESTOSTERONE UNDECANOATE COMPOSITIONS AND USE THEREOF

FIELD OF THE INVENTION

The present invention relates to testosterone undecanoate containing pharmaceutical compositions, dosing regimens therefor, and criteria for the continuation and discontinuation thereof. Accordingly, this invention involves the fields of chemistry, pharmaceutical sciences, medicine and other health sciences.

BACKGROUND OF THE INVENTION

Male hypogonadism is a serious condition affecting mostly aging men. The common reasons for hypogonadism in men could be physiological abnormality involving among other factors, improper functioning or growth of the gonads and/or the pituitary-hypothalamus regulatory systems, and aging. Many of the abnormalities that are identified to be commonly associated with the low or decreased testosterone levels include impaired sexual function and/or libido, metabolic syndrome which may be a combination of abdominal obesity, high blood pressure, insulin resistance, lipid disorders; high risk of cardiovascular diseases; reduced bone mass/mineral density and muscle weakness and or degeneration affecting the musculoskeletal system. Other effects of low testosterone levels include negative changes in body composition, depression and other psychological disorders. Various compositions and methods for treating low testosterone levels are taught in the following US patents and applications, all of which are expressly incorporated herein in their entirety by this reference: U.S. Pat. Nos. 8,778,922, 8,865,695, 9,943,527, 9,949,985, 10,2264,73, 10,716,794, 2018/0333422, 2018/0147215, and 2019/0240236.

It is recognized that the normal range of serum total testosterone (T) in a healthy adult man is based on the laboratory normal range in clinical studies (typically from about 300 ng/dL to about 1080 ng/dL) and this range is named as the eugonadal range (or therapeutically effective amount range of serum T levels). Restoration of testosterone levels to the eugonadal range generally corrects many of the cited clinical abnormalities associated with hypogonadism or improves conditions and symptoms of any other diseases induced by low testosterone levels.

While oral administration is the most preferred and patient friendly route for administration of testosterone, the effective oral delivery of testosterone has been a challenge due to extremely poor bioavailability of testosterone, which has required very high dosing as well as frequent dosing due to the short serum half-life. These problems with orally administered testosterone products are primarily due to first pass metabolism. In addition, excessive direct oral delivery of testosterone has also been known to cause enzyme induction resulting in potential drug-drug interactions and its excessive prolonged use, such as oral administration of methyltestosterone, has in some cases been limited because of the development of liver disease, such as peliosis hepatis, hepatic neoplasms, hepatocellular carcinoma cholestatic hepatitis, and jaundice. Thus, there is a need for a means to avoid under administration and over administration of testosterone.

To enable effective oral Testosterone Replacement Therapy (TRT) comprising a testosterone ester, each patient's testosterone (T) levels after treatment should be measured to ensure the patient is restored to within therapeutically effective T levels. In clinical use of oral testosterone undecanoate (TU) treatment, a single serum total T concentration after oral dose administration measured at a specific time point (a single hour time point) is used to monitor effectiveness of the TRT. Labels of currently marketed oral TU TRT products, such as JATENZO in US and ANDRIOL Testocaps outside the US, recommended a dosing regimen for effective T restoration that entails dose adjustments (or titration) for individual patients based on treatment response in T level. For example, JATENZO requires dose titration, where the minimum recommended dose is 158 mg twice daily and the maximum recommended dose is 396 mg (two 198 mg capsules) twice daily per JATENZO label instructions. In the study CLAR-15012 with JATENZO, only 26% of the patients receiving JATENZO at starting dose of 237 mg TU BID achieved effective T levels at steady state without requiring dose adjustment (see: https://www.jatenzo.com/hcp/oral-dosing/). Per label instructions for ANDRIOL Testocaps, the dosage of ANDRIOL should be determined by the physician according to the severity of the symptoms (see: https.//www.medsafe.govt.nz/Consumers/cmi/a/andriol/pdf). The initial dose is usually 120-160 mg/day for 2-3 weeks. Subsequent dosages (40-120 mg/day) should also be based on the clinical effect obtained in the first weeks of the therapy.

The JATENZO label advises periodic monitoring of serum testosterone concentrations at 6 hours after a morning dose with no specific provision for discontinuation of treatment of JATENZO for patients who are poor efficacy responders (poor responders) to JATENZO (T levels consistently below the target lower limit of serum T levels, <425 ng/dL) after required dose adjustments, if any. Moreover Bhasin et al., in "Testosterone Therapy in Men with Androgen Deficiency Syndromes: An Endocrine Society Clinical Practice Guideline", J. Clin. Endocrinol. Metab., 95:2536-2559, 2010, described that the regimen for administration of oral TU is to take 40 to 80 mg orally, twice daily or three times daily with meals (i.e., 80 mg to 240 mg total daily dose) with measuring serum T level at 3 to 5 hours after ingestion (see: https.//pubmed.ncbi.nlm.nih.gov/20525905/).

For oral BID products, measuring of T levels at times prior to T $C_{max}$ (reported to typically occur 6 hours or less after dose administration) is prone to result in higher intra/inter subject variability in T measurements, and errors in continuation decisions for effectiveness. Such errors are likely due to possible steep increases in T levels related to significant ongoing absorption as compared to T levels measured after T $C_{max}$.

Therefore, there exists a need to develop oral TU compositions, dosing regimens with more reliable monitoring for continued use, and methods for administration thereof having assessment of measured T values so as to enable effective T restoration with proper continuation criteria and discontinuation criteria for both poor responders and super responders.

Moreover, there also exists a need to develop oral TU compositions, dosing regimen, and methods that are easy to prescribe and easy to use so as to enable therapeutically effective T restoration without a need for dose adjustment in the majority of patients.

SUMMARY OF THE INVENTION

The present disclosure is drawn to effective fixed dose oral TU compositions and methods for treatment of patients in need of TRT.

In an embodiment, a TU pharmaceutical composition is used in restoring a therapeutically effective level of T concentration in a hypogonadal male subject in response to an oral administration regimen thereof, and wherein said composition performance includes monitoring with a continuation criteria comprising a single serum T concentration level measured at a steady state at a predetermined number of weeks after initiation of said regimen and at a predetermined number of hours after administering a morning dose of said regimen.

In an embodiment, a TU pharmaceutical composition for use in restoring a therapeutically effective level of T concentration in a hypogonadal male subject in response to an oral administration regimen thereof, and wherein the composition includes a criteria for monitoring for continued use or discontinuation which advises to: "Monitor serum testosterone (8 to 9 hours after the morning dose) 3 to 4 weeks after initiating the TU pharmaceutical composition, and periodically thereafter. Based on serum testosterone measurements, determine if TU pharmaceutical composition should be continued or discontinued according to the following criteria: If serum testosterone is 300-1080 ng/dL, continue TU pharmaceutical composition, If serum testosterone is <300 ng/dL, discontinue TU pharmaceutical composition, and If serum testosterone >1080 ng/dL, discontinue TU pharmaceutical composition".

In further embodiment, an oral TU pharmaceutical composition to restore therapeutically effective T levels in hypogonadal males comprises a 225 mg BID (twice daily) fixed dose regimen (i.e. without dose adjustment), wherein said composition performance includes monitoring with a continuation criteria comprising a single serum T concentration level measured at a steady state at a predetermined number of weeks after initiation of said regimen and at a predetermined number of hours after administering a morning dose of said regimen.

In further embodiment, an oral TU pharmaceutical composition to restore therapeutically effective T levels in hypogonadal males comprises a 225 mg BID fixed dose regimen, and wherein said composition performance includes monitoring with a continuation criteria comprising a single serum T concentration level measured at a steady state at a predetermined number of weeks after initiation of said regimen and periodically thereafter, at a predetermined number of hours after administering a morning dose of said regimen.

In some embodiments, an oral TU pharmaceutical composition to restore therapeutically effective T levels in hypogonadal males comprises a 225 mg BID fixed dose regimen, and wherein said composition performance includes monitoring with a continuation criteria comprising a single serum T concentration level measured at a steady state at 3 to 4 weeks after initiation of said regimen and periodically thereafter, at a predetermined number of hours after administering a morning dose of said regimen.

In some embodiments, an oral TU pharmaceutical composition to restore therapeutically effective T levels in hypogonadal males comprises a 225 mg BID fixed dose regimen, and wherein said composition performance includes monitoring with a continuation criteria comprising a single serum T concentration level measured at a steady state at 3 to 4 weeks after initiation of said regimen and periodically thereafter, at 8 to 9 hours after administering a morning dose of said regimen.

In a specific embodiment, an oral TU pharmaceutical composition to restore a therapeutically effective T concentration in a hypogonadal male subject in response to a 225 mg BID fixed dose oral administration regimen thereof, wherein said composition performance includes monitoring with a continuation criteria comprising a single serum T concentration level measured at a steady state at 3 to 4 weeks after initiation of said regimen and periodically thereafter, and 8 to 9 hours after administering a morning dose of said regimen, wherein if said measured single serum T concentration level is within a range of 300 ng/dL to 1080 ng/dL, said regimen is continued, and wherein if said single serum T concentration level is not within a range of 300 ng/dL to 1080 ng/dL, said regimen is discontinued.

In an embodiment, a method of continuing or discontinuing a fixed dose oral administration regimen of a pharmaceutical composition having TU comprises continuing said regimen if a single serum T concentration level measured at a steady state a predetermined number of weeks after initiation of said regimen and a predetermined number of hours after administration of a morning dose of said regimen is within predetermined range and discontinuing said regimen if a single serum T concentration level measured at a steady state a predetermined number of weeks after initiation of said regimen and a predetermined number of hours after administration of a morning dose of said regimen is not within said predetermined range.

In an embodiment, a method of continuing or discontinuing a fixed dose oral administration regimen of a pharmaceutical composition having 225 mg BID (450 mg daily) of TU comprising continuing said regimen if a single serum T concentration level measured at a steady state a predetermined number of weeks after initiation of said regimen and periodically thereafter, and a predetermined number of hours after administration of a morning dose of said regimen is within predetermined range and discontinuing said regimen if a single serum T concentration level measured at a steady state a predetermined number of weeks after initiation of said regimen and a predetermined number of hours after administration of a morning dose of said regimen is not within said predetermined range.

In an embodiment, a method of continuing or discontinuing a fixed dose oral administration regimen of a pharmaceutical composition having 225 mg BID (450 mg daily) of TU comprising continuing said regimen if a single serum T concentration level measured at a steady state a predetermined number of weeks after initiation of said regimen and periodically thereafter, and a predetermined number of hours after administration of a morning dose of said regimen is within a range of 300 ng/dL to 1,080 ng/dL and discontinuing said regimen if a single serum T concentration level measured at a steady state a predetermined number of weeks after initiation of said regimen and a predetermined number of hours after administration of a morning dose of said regimen is not within a range of 300 ng/dL to 1,080 ng/dL.

In another specific embodiment, a method of continuing or discontinuing a fixed dose oral administration regimen having a 225 mg BID TU pharmaceutical composition comprising:

initiating said regimen to a hypogonadal male subject having a testosterone concentration below 300 ng/dL;

measuring a steady state single serum T concentration level 8 to 9 hours after administration of a morning dose of said regimen three to four weeks after initiation of said regimen and periodically thereafter; and continuing said regimen if said measurement is within a range of 300 ng/dL to 1,080 ng/dL and discontinuing said regimen if said measurement is not within a range of 300 ng/dL to 1,080 ng/dL.

DETAILED DESCRIPTION

Before invention embodiments are described, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular examples or embodiments only and is not intended to be limiting.

Furthermore, the described features, structures, or characteristics can be combined in any suitable manner in one or more embodiments. In the following description, numerous specific details are provided, such as examples of compositions, dosage forms, treatments, etc., to provide a thorough understanding of various invention embodiments. One skilled in the relevant art will recognize, however, that such detailed embodiments do not limit the overall inventive concepts articulated herein, but are merely representative thereof.

It should be noted that, the singular forms "a," "an," and, "the" include plural referents unless the context clearly dictates otherwise. Thus, for example, reference to "an excipient" includes reference to one or more of such excipients, and reference to "the carrier" includes reference to one or more of such carriers.

As used herein, "AUC" refers to the area under the serum concentration-time curve.

As used herein, "AUCt" refers to the area under the serum concentration-time curve from time zero to time of last measurable concentration.

As used herein, "$C_{avg}$" refers to average serum concentration over 24 hours.

As used herein, "$C_{max}$" refers to maximum observed serum concentration per dose overdosing interval.

As used herein, "hypogonadism" means any condition wherein serum testosterone is below the normal eugonadal range, such as 300 ng/dL when measured on two separate occasions in the morning. In another definition, the oral TU composition described herein can be used to treat patients that are eugonadal (or hypogonadal) for a condition other than specifically having testosterone levels lower than 300 ng/dL. In another specific definition, the oral TU therapy refers to testosterone replacement therapy e.g., to treat a condition associated with a deficiency or absence of endogenous testosterone.

As used herein, "eugonadal range" and "normal range" are used interchangeably and are the typical range of serum testosterone found in patients not needing TU. For example, normal or eugonadal range is defined as the range with an average testosterone lower limit of ~300 ng/dL and average testosterone upper limit of the lab reference range, such as 1080 ng/dL used in this invention. It is understood that this normal range could vary depending on the testosterone assay utilized and variability among labs due to a specific assay used by an individual lab and patient demographics. Therefore, the lower limit of normal eugonadal range could also be 250 ng/dL. Similarly, the upper limit of normal eugonadal range could be 1000 or 1100, or 1500 ng/dL. In an aspect, "predetermined range for evaluation of efficacy for TRT" is interchangeably used with "normal range" and "eugonadal range".

As used herein, " " refers to a patient having serum T concentration, measured at a predetermined time after morning dose, more specifically 8 to 9 hours after a morning dose, in 3 to 4 weeks after initiation of the treatment, that is deemed effective such as within the normal range (e.g., within 300 ng/dL to 1080 ng/dL).

As used herein, "poor responder" refers to a patient having serum T concentration measured at a predetermined time after morning dose, and more especially 8 to 9 hours after a morning dose in 3 to 4 weeks after initiation of treatment, deemed ineffective such as below 300 ng/dL upon periodically monitoring, and "super responder" refers to a patient having serum T concentration measured at a predetermined time after morning dose, more specifically 8 to 9 hours after a morning dose in 3 to 4 weeks after initiation of the treatment, deemed supra-physiological such as above the ULN (Upper Limit of Normal) (e.g., 1080 ng/dL) upon periodically monitoring. As used herein, "non-responder" can refer to either or both of poor responders and super responders.

As used herein, "dose", "dosing regimen", and "administration regimen" can be used interchangeably and refer to specific dosing and oral administration of a TU containing product. In a specific embodiment, the dosing regimen typically entails daily dose, number of pills per dose, number of doses per day, and whether or not to take with food or fasting. The dosing regimen can also provide relevant instructions regarding the above, for healthcare providers and patients, in some embodiments. Some products (but not the product described herein) involve dose titration or a dose adjustment scheme, in patients needing adjustment, based on a patient's response to the product assessed via measured single serum T levels after dosing at steady state. A practical dosing regimen is the one that is easy to comprehend for implementation. The specific dosing regimen of this invention is a single fixed dose dosing regimen for oral TU—i.e. a dosing regimen that does not need dose titration (dose adjustment).

As used herein, "fixed dose", "without dose adjustment", "without titration", "untitrated", and "without dose titration" are used interchangeably and refer to the same (e.g. unchanging) daily dose of oral TU being used for each patient throughout a therapy regimen with no dose changes. "Single," "singular" or "unitary" fixed dose means that only one fixed daily dose (e.g., as described herein elsewhere like one of 450 mg TU per day) of TU is prescribed to a patient. No dose adjustment needed (or without dose titration) means for a given patient, the daily TU dose is not adjusted throughout the therapy.

As used herein, "periodically" refers to at least two or more times or occurrences as measured on two separate occasions at least 3-4 weeks apart.

In this application, "comprises", "comprising", "containing", and "having" and the like can have the meaning ascribed to them in U.S. patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. patent law. "Consisting essentially of" or "consists essentially of" have the meaning generally ascribed to them by U.S. patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open-ended term, like "comprising" or "including," in this written description it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

As used herein, "subject" or "patient" are used interchangeably and refer to a mammal that may benefit from the administration of a composition described herein. In one aspect, the mammal is a human. In another aspect, the mammal is a human male.

As used herein, the terms "formulation" and "composition" are used interchangeably and refer to a mixture of two or more compounds, elements, or molecules. In some aspects, the terms "formulation" and "composition" are used to refer to a mixture of one or more active agents with a carrier or other excipients. Compositions can take nearly any physical state, including solid and/or liquid (i.e. solution). Furthermore, the term "dosage form" can include one or more formulation(s) or composition(s) provided in a form suitable for administration to a subject.

As used herein, "effective amount" refers to an amount of an ingredient which, when included in a composition, is sufficient to achieve an intended compositional or physiological effect. For example, "effective T concentration" refers to "therapeutically effective amount", which is within the eugonadal range of serum T concentration. Thus, a "therapeutically effective amount" refers to a substantially non-toxic, but sufficient amount of an active agent, to achieve therapeutic results in treating or preventing a condition for which the active agent is known to be effective. It is understood that various biological factors may affect the ability of a substance to perform its intended task. Therefore, an "effective amount" or a "therapeutically effective amount" may be dependent in some instances on such biological factors. Additionally, in some cases an "effective amount" or a "therapeutically effective amount" may not be achieved in a single dose. Rather, in some examples, an "effective amount" or a "therapeutically effective amount" can be achieved after administering a plurality of doses over a period of time, such as in a pre-designated dosing regimen. Further, while the achievement of therapeutic effects may be measured by a physician or other qualified medical person using evaluations known in the art, it is recognized that individual variation and response to treatments may make the achievement of therapeutic effects a subjective decision. The determination of an effective amount is well within the ordinary skill in the art of pharmaceutical and nutritional sciences as well as medicine.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 mg to about 80 mg" should also be understood to provide support for the range of "50 mg to 80 mg." Furthermore, it is to be understood that in this written description support for actual numerical values is provided even when the term "about" is used therewith. For example, the recitation of "about" 30 should be construed as not only providing support for values a little above and a little below 30, but also for the actual numerical value of 30 as well.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, levels, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-2, from 1-3, from 1-4, from 2-3, from 2-4, from 2-5, from 3-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Reference in this application may be made to compositions, systems, or methods that provide "improved" or "enhanced" performance. It is to be understood that unless otherwise stated, such "improvement" or "enhancement" is a measure of a benefit obtained based on a comparison to compositions, systems or methods in the prior art. Furthermore, it is to be understood that the degree of improved or enhanced performance may vary between disclosed embodiments and that no equality or consistency in the amount, degree, or realization of improvement or enhancement is to be assumed as universally applicable.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

It is noted that testosterone levels can be monitored via a variety of testosterone assays. Such testosterone assays (e.g., for serum testosterone, total testosterone, free testosterone etc.) can be performed as part of a diagnosis of hypogonadism, a treatment efficacy assessment, or discontinuation of therapy. The assays themselves can be radioimmunoassays via commercial kits, validated mass spectrometric methods, or any other suitable assay.

As used herein, the terms "treatment" and "therapy" are used interchangeably when used in conjunction with the administration of pharmaceutical compositions and oral dosage capsules containing TU, and refer to the administration of the oral dosage capsules and pharmaceutically acceptable composition to subjects who are either asymptomatic or symptomatic. In other words, "treatment" and "therapy" can both be to reduce or eliminate symptoms associated with a condition present in a subject, or it can be prophylactic treatment, i.e. to prevent the occurrence of the symptoms in a subject. Such prophylactic treatment can also be referred to as prevention of the condition.

As used herein, "steady state" refers to the achievement of a stable response in serum total testosterone levels to exogenously administered testosterone undecanoate, typically achieved after at least one week following the start of a dosing regimen.

As used herein, "titration visit" and "T monitoring visit" are used interchangeably and refer to the visit on when single serum T concentration measurement is required for titration, if any, or decision of continuation and discontinuation for therapy due to non-effectiveness. It should be noted that one or more titration visits (or T monitoring visits), if titration is required, can be conducted to ensure patient within the normal range of serum T concentration.

As used herein, the average serum testosterone concentration can be determined using methods and practices known in the art. For example, the average baseline plasma testosterone concentration of a human male is the arithmetic mean of the total plasma testosterone concentrations determined on at least two consecutive time points that are reasonably spaced from each other, for example from about 1 hour to about 168 hours apart. In a particular case, the testosterone concentration can be determined on at least two consecutive times that are about 12 hours to about 48 hours apart. In another particular method, the testosterone concentration of the human male for diagnosing hypogonadism can be determined at a time between about 5 o'clock and about 11 o'clock in the morning. Further, the testosterone concentration can be the determined by standard analytical procedures and methods available in the art, such as for example, automated or manual immunoassay methods, liquid chromatography or liquid chromatography-tandem mass spectrometry (LC-MSMS) etc.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, variants, modifications, and equivalents as may be included within the spirit and scope of the invention as defined by the appended claims.

In an embodiment, the present findings are drawn to effective oral TU pharmaceutical compositions and methods for treatment of patients in need of TRT using the continuation/discontinuation criteria with single serum T concentration measurement.

In another embodiment, the present findings are drawn to effective fixed dose oral TU pharmaceutical compositions and methods for treatment of patients in need of TRT using the continuation/discontinuation criteria with single serum T concentration measurement.

In further embodiment, the findings are related to an oral TU pharmaceutical composition, to restore effective T levels in hypogonadal males, comprising a 225 mg BID (450 mg daily) fixed dose and its regimen methods comprising continuation/discontinuation criteria by monitoring single serum T concentration measured 8 to 9 hours after a morning dose at 3 to 4 weeks after initiating the oral TU composition, and periodically thereafter. Based on monitored serum testosterone measurements, the regimen is continued or discontinued according to the following criteria:

Measured serum testosterone is in the range of 300-1080 ng/dL: the regimen is continued;

Measured serum testosterone is <300 ng/dL: the regimen is discontinued; and

Measured serum testosterone is >1080 ng/dL: the regimen is discontinued.

In an aspect, the criteria of continuing and discontinuing the regimen via single serum T concentration were established by comparing the single serum T concentration measured at each single hour after a morning dose with the T $C_{avg}$ calculated from intensive T Pharmacokinetic (PK) data.

In another aspect, the finding demonstrates that the (normal) responder rate for continuing the oral TU regimen at the first visit by single serum T measurement at 8 to 9 hours after a morning dose at the steady state after initiation of the fixed 225 mg BID oral TU composition regimen is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100%.

In a specific aspect, the finding demonstrates that the (normal) responder rate for continuing the oral TU therapy at the first visit by single serum T measurement at 8 to 9 hours after a morning dose at 3 to 4 weeks (steady state) after initiation of the fixed 225 mg BID oral TU composition regimen is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100%.

In further embodiment, certain non-responders, (i.e. those who had a single serum T concentration outside the normal range of T<300 ng/dL or T>1,080 ng/dL), at the first visit were re-visited to confirm to continue or discontinue the oral TU therapy with the 225 mg BID fixed dose without titration. Thus for example, a patient who had T concentration less than one of 300 ng/dL, 250 ng/dL, 200 ng/dL, 150 ng/dL, or 100 ng/dL, revisited to confirm continuing the oral TU therapy if the patient has single serum T concentration within the normal range (300 ng/dL≤T≤1080 ng/dL) at the second visit or discontinuing the oral TU therapy if the patient has single serum T concentration outside the normal range (T<300 ng/dL or T>1,080 ng/dL) at the second visit.

In the specific aspect of an embodiment, the findings showed that percentage of the non-responders at the first visit determined by single serum T measurement at 8 to 9 hours after a morning dose of the fixed 225 mg BID oral TU composition was approximately 29% but could be approximately 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, and 0% of the population. Patients revisited and were assessed to confirm to continue or discontinue the oral therapy by monitoring single serum T concentration measured 8 to 9 hours after a morning dose at the second visit.

In the specific aspect of an embodiment, the oral TU composition disclosed herein comprising the fixed 225 mg BID (450 mg daily) regimen of TU without titration can provide the concordance for continuation of the therapy with at least 84%, 85%, 86%, 87%, 88%, 89%, 90%, 91%, 92%, 93%, 94%, 95%, 96%, 97%, 98%, 99%, and 100% by periodically (at the steady state) monitoring single serum T concentration measured at 8 to 9 hours after a morning dose and at least 3 to 4 weeks after initiation of the therapy.

In an embodiment, based on the continuation/discontinuation criteria assessment in the clinical study, it was found that the oral TU pharmaceutical composition disclosed herein is effective in restoring a therapeutically effective T concentration in a hypogonadal male subject in response to an oral administration regimen thereof, and wherein said composition performance includes monitoring with a continuation criteria comprising a single serum T concentration level measured at a steady state a predetermined number of weeks after initiation of said regimen and a predetermined number of hours after administering a morning dose of said regimen.

In another embodiment, in a TU pharmaceutical composition disclosed herein is used for restoring a therapeutically effective amount of T concentration in a hypogonadal male subject in response to an oral administration regimen thereof, said composition performance includes monitoring with a continuation criteria comprising a single serum T concentration level measured at a steady state a predetermined number of weeks after initiation of said regimen and periodically thereafter, and a predetermined number of hours after administering a morning dose of said regimen.

In further embodiment, in an oral TU pharmaceutical composition to restore a therapeutically effective T levels in hypogonadal males comprises a 225 mg BID (twice daily) fixed dose regimen without dose adjustment, said composition performance includes monitoring with a continuation criteria comprising a single serum T concentration level measured at a steady state a predetermined number of weeks after initiation of said regimen and a predetermined number of hours after administering a morning dose of said regimen.

In some embodiments, in an oral TU pharmaceutical composition to restore a therapeutically effective T levels in hypogonadal males comprises a 225 mg BID (twice daily) fixed dose regimen without dose adjustment, said composition performance includes monitoring with a continuation criteria comprising a single serum T concentration level measured at a steady state a predetermined number of weeks after initiation of said regimen and periodically thereafter, and a predetermined number of hours after administering a morning dose of said regimen.

In some embodiments, in an oral TU pharmaceutical composition to restore a therapeutically effective T levels in hypogonadal males comprises a 225 mg BID (twice daily) fixed dose regimen without dose adjustment, said composition performance includes monitoring with a continuation criteria comprising a single serum T concentration level measured at a steady state a 3 to 4 weeks after initiation of the oral TU composition and a predetermined number of hours after administering a morning dose of said regimen.

In some embodiments, in an oral TU pharmaceutical composition to restore a therapeutically effective T levels in hypogonadal males comprises a 225 mg BID (twice daily) fixed dose regimen without dose adjustment, said composition performance includes monitoring with a continuation criteria comprising a single serum T concentration level measured at a steady state a 3 to 4 weeks after initiation of the oral TU composition and periodically thereafter, and a predetermined number of hours after administering a morning dose of said regimen.

In some embodiments, in an oral TU pharmaceutical composition to restore a therapeutically effective T levels in hypogonadal males comprises a 225 mg BID (twice daily) fixed dose regimen without dose adjustment, said composition performance includes monitoring with a continuation criteria comprising a single serum T concentration level measured at a steady state a 3 to 4 weeks after initiation of the oral TU composition and periodically thereafter, and a 8 to 9 hours after administering a morning dose of said regimen.

In a specific embodiment, in an oral TU pharmaceutical composition for restoring a therapeutically effective amount of T concentration in a hypogonadal male subject in response to a 225 mg BID (twice daily) fixed dose oral administration regimen thereof, said composition performance includes monitoring with a continuation criteria comprising a single serum T concentration level measured at a steady state a 3 to 4 weeks after initiation of said regimen and periodically thereafter, and 8 to 9 hours after administering a morning dose of said regimen, wherein if said single serum T concentration level is within a range of 300 ng/dL to 1080 ng/dL, said regimen is continued, and wherein if said single serum T concentration level is not within a range of 300 ng/dL to 1080 ng/dL, said regimen is discontinued.

In an embodiment, a method of continuing or discontinuing a fixed dose oral administration regimen of a pharmaceutical composition having TU comprises continuing said regimen if a single serum T concentration level measured at a steady state a predetermined number of weeks after initiation of said regimen and a predetermined number of hours after administration of a morning dose of said regimen is within predetermined range and discontinuing said regimen if a single serum T concentration level measured at a steady state a predetermined number of weeks after initiation of said regimen and a predetermined number of hours after administration of a morning dose of said regimen is not within said predetermined range.

In an embodiment, a method of continuing or discontinuing a fixed dose oral administration regimen of a pharmaceutical composition having TU comprises continuing said regimen if a single serum T concentration level measured at a steady state a predetermined number of weeks after initiation of said regimen and periodically thereafter, and a predetermined number of hours after administration of a morning dose of said regimen is within predetermined range and discontinuing said regimen if a single serum T concentration level measured at a steady state a predetermined number of weeks after initiation of said regimen and a predetermined number of hours after administration of a morning dose of said regimen is not within said predetermined range.

In an embodiment, a method of continuing or discontinuing a fixed dose oral administration regimen of a pharmaceutical composition having TU comprises continuing said regimen if a single serum T concentration level measured at a steady state a predetermined number of weeks after initiation of said regimen and periodically thereafter, and a predetermined number of hours after administration of a morning dose of said regimen is within a range of 300 ng/dL to 1,080 ng/dL and discontinuing said regimen if a single serum T concentration level measured at a steady state a predetermined number of weeks after initiation of said regimen and a predetermined number of hours after administration of a morning dose of said regimen is not within a range of 300 ng/dL to 1,080 ng/dL.

In a specific embodiment, a method of continuing or discontinuing a fixed dose oral administration regimen of a TU pharmaceutical composition comprises:

initiating said regimen for a hypogonadal male subject having a testosterone concentration below 300 ng/dL;

measuring a steady state single serum T concentration level 8 to 9 hours after administration of a morning dose of said regimen three to four weeks after initiation of said regimen; and continuing said regimen if said measurement is within a range of 300 ng/dL to 1,080 ng/dL and discontinuing said regimen if said measurement is not within a range of 300 ng/dL to 1,080 ng/dL.

In another specific embodiment, a method of continuing or discontinuing a fixed dose oral administration regimen having a 225 mg BID (twice daily) TU pharmaceutical composition comprises:

initiating said regimen for a hypogonadal male subject having a testosterone concentration below 300 ng/dL;

measuring a steady state single serum T concentration level 8 to 9 hours after administration of a morning dose of said regimen three to four weeks after initiation of said regimen and periodically thereafter; and continuing said regimen if said measurement is within a range of 300 ng/dL to 1,080 ng/dL and discontinuing said regimen if said measurement is not within a range of 300 ng/dL to 1,080 ng/dL.

Specific Pharmaceutical Compositions and Formulations

As disclosed herein, one embodiment is a pharmaceutical composition comprising TU for treatment of subjects in testosterone therapy. The pharmaceutical composition comprises orally administering a therapeutically effective amount of a testosterone ester, such as TU, to the patient via an oral dosage form. The oral dosage form can be administered to the patient in a fixed dose dosing regimen.

In an aspect, the pharmaceutical composition comprises oral administration of a therapeutically effective amount of TU twice per day with food. In one aspect, the pharmaceutical composition comprises oral administration of TU in a single fixed dose dosing regimen which provides from about 400 mg to 475 mg of TU per day. In one aspect, the pharmaceutical composition comprises oral administration of TU in a single fixed dose dosing regimen which provides from about 420 mg to 460 mg of TU per day. In one aspect, the pharmaceutical composition comprises oral administration of TU in a fixed dose dosing regimen which provides from 450 mg of TU administered twice daily.

As disclosed herein, one embodiment is a pharmaceutical composition for restoring average testosterone levels to a normal eugonadal range while avoiding unacceptably high serum testosterone levels in patients needing TU. The pharmaceutical composition can be used in administering a therapeutically effective amount of a testosterone ester to a patient via an oral dosage form using a fixed dose dosing regimen. In one aspect, the pharmaceutical composition can be used in oral administration of a therapeutically effective amount of TU to a patient in need of treatment via a single fixed dose dosing regimen. In one aspect, the pharmaceutical composition can be used in oral administration of a therapeutically effective amount of TU once or twice per day in a fixed dose dosing regimen of TU. In one aspect, the pharmaceutical composition can be used in oral administration of a therapeutically effective amount of TU once or twice per day with food. In one aspect, the pharmaceutical composition can be used in oral administration of TU in a single fixed dose dosing regimen which provides from about 420 mg to 460 mg of TU per day. In one aspect, the pharmaceutical composition can be used in oral administration of TU in a fixed dose dosing regimen which provides from 450 mg of TU administered twice daily.

As disclosed herein, one embodiment is a pharmaceutical composition for restoring T $C_{avg}$ to a normal range by administering TU in an oral dosage form using a dosing regimen that does not need dose adjustment or titration and that provides at least a daily dose of 300 mg of TU per day and wherein at least 75% of the patients (e.g., in a population of patients or subjects where the population is 10 or more, 20 or more, 30 or more, 40 or more, 50 or more, 60 or more, 70 or more, 80 or more, 90 or more or 100 or more patients or subjects) treated using the dosing regimen described herein achieve T $C_{avg}$ within the normal range. In one aspect, a method of using the pharmaceutical composition comprises oral administration of a therapeutically effective amount of TU to a patient in need of treatment via a fixed dose dosing regimen. In one aspect, a method of using the pharmaceutical composition comprises oral administration of a therapeutically effective amount of TU once or twice per day in a fixed dose dosing regimen of TU. In one aspect, a method of using the pharmaceutical composition comprises oral administration of a therapeutically effective amount of TU once or twice per day with food. In one aspect, a method of using the pharmaceutical composition comprises oral administration of TU in a single fixed dose dosing regimen which provides from about 300 mg to 600 mg of TU per day. In one aspect, a method of using the pharmaceutical composition comprises oral administration of TU in a single fixed dose dosing regimen which provides from about 400 mg to 475 mg of TU per day. In one aspect, a method of using the pharmaceutical composition comprises oral administration of TU in a fixed dose dosing regimen which provides from about 420 mg to 460 mg of TU administered twice daily. In one aspect, a method of using the pharmaceutical composition comprises oral administration of TU in a fixed dose dosing regimen which provides 450 mg of TU administered twice daily.

As disclosed herein, one embodiment is a pharmaceutical composition for restoring testosterone levels in a patient needing TU to within normal T levels while avoiding unacceptably high T levels. A method of using the pharmaceutical composition can include administering TU via an oral dosage form using a dosing regimen that does not need a dose adjustment or titration and that provides a daily amount of TU of about 300-600 mg.

As disclosed herein, one embodiment is a pharmaceutical composition for restoring testosterone levels in a patient needing TU to within normal T levels while avoiding unacceptably high T levels. A method of using the pharmaceutical composition can include administering TU via an oral dosage form using a dosing regimen that does not need a dose adjustment or titration and that provides a daily amount of TU of about 400-475 mg.

As disclosed herein, one embodiment is a pharmaceutical composition of restoring testosterone levels in a patient needing TU to within normal T levels while avoiding unacceptably high T levels. A method of using the pharmaceutical composition can include administering TU via an oral dosage form using a dosing regimen that does not need a dose adjustment or titration and that provides a daily amount of TU of about 420-460 mg.

As disclosed herein, one embodiment is a pharmaceutical composition of restoring testosterone levels in a patient needing TU to within normal T levels while avoiding unacceptably high T levels. A method of using the pharmaceutical composition can include administering TU via an oral dosage form using a dosing regimen that does not need a dose adjustment or titration and that provides a daily amount of TU of about 450 mg.

The oral testosterone replacement therapy described herein was discovered to be safe and efficacious. It is believed that the oral TU therapy with a fixed dose regimen without titration disclosed herein meets at least one of the following criteria when used in a sufficient population of individuals needing such therapy (e.g., hypogonadal men):

(1) Proportion of subjects with T $C_{avg}$ within the normal range (e.g., 300-1080 ng/dL) is: at least ≥75%, 77%, 79%, 81%, 83%, 85%, 86%, 87%, 88%, 89%, 90%, 91%, 92%, 93%, 94%, 95% or more;

(2) Proportion of subjects with T $C_{avg}$ within the normal range is: at least ≥65%, 67%, 69%, 71%, 73%, 75%, 76%, 77%, 78%, 79%, 80%, 81%, 82%, 83%, 84%, 85% or more for a lower bound 95% CI (Confidence Interval);

(3) Proportion of subjects with T $C_{max}$ outside the normal range ($C_{max}$≥1.5×ULN (e.g., 1,620 ng/dL)) is: no greater than 15%, 16%, 17%, 18%, 19% 20%, 21%, 22%, 23%, 24% or 25%;

(4) Proportion of subjects with T $C_{max}$ between 1.8×ULN (e.g., 1,944 ng/dL) and 2.5×ULN (e.g., 2,720 ng/dL) is: no greater than 5% 6%, 7%, 8%, 9% or 10%; and (5) Proportion of subjects with T $C_{max}$>2.5×ULN (e.g., 2,720 ng/dL) is: 0%, or no greater than 1%, 2%, 3%, 4% or 5%.

In some embodiments, testosterone concentrations (e.g., blood, serum, or plasma) can be checked periodically, e.g., 8-9 hours after a morning dose, starting as soon as three to four weeks after initiating treatment with oral TU. When the total testosterone concentration consistently exceeds ULN (1080), 1100, 1200, 1300, 1400, 1500, 1600, 1700, 1800, 1900, 2000, 2100, 2200, 2300, 2400, 2500, 2600, 2700, or 2720 ng/dL, therapy with oral TU can be considered as potentially discontinuation as advised by trained medical personnel. If the total testosterone concentration is consistently below 300 ng/dL, an alternative treatment can be considered as advised by trained medical personnel.

In another embodiment, testosterone concentrations (e.g., blood, serum, or plasma) can be checked periodically, e.g., 8-9 hours after a morning dose, starting as soon as three to four weeks after initiating treatment with an oral TU composition without dose titration. If the total testosterone concentration consistently exceeds 2.5×ULN (e.g., 2720 ng/dL), therapy with the oral TU composition can be discontinued as advised by trained medical personnel. If the total testosterone concentration is consistently below 300 ng/dL, an alternative treatment can be considered as advised by trained medical personnel. As used in this paragraph, "consistently" can refer to two or more times or occurrences at a similar time point in a separate day.

In some examples, oral TU continuation/discontinuation criteria are assessed at steady state, approximately after at least 2 weeks after initiation of the oral TU therapy.

In some examples, oral TU continuation/discontinuation criteria are assessed at steady state, approximately after at least 2 weeks after initiation of the oral TU therapy, by measuring single serum testosterone concentrations.

In some examples, oral TU continuation/discontinuation criteria are assessed at steady state, approximately after at least 2 weeks after initiation of the oral TU therapy, by measuring single serum testosterone concentrations at 8 to 9 hours after a morning dose after a fixed dose administration of the oral TU.

In some examples, oral TU continuation/discontinuation criteria are assessed at steady state, approximately after at least 2 weeks after initiation of the oral TU therapy, by measuring single serum testosterone concentrations at 8 to 9 hours after a morning dose after a 225 mg fixed dose administration of the oral TU.

In one embodiment, a pharmaceutical composition comprises orally administering a dosage form of that comprises TU and a carrier including a pharmaceutically acceptable additive. The pharmaceutically acceptable additives comprise one or more lipophilic additives, one or more hydrophilic additives, other suitable pharmaceutically acceptable additives, and a combination thereof.

Thus, in some embodiments, orally administered TU compositions can be used in the following exemplary replacement therapies described below or previously in this specification.

In one example, a testosterone replacement therapy for a male patient having a condition associated with a deficiency or absence of endogenous testosterone comprises orally administering a fixed dose of a therapeutically effective amount of TU to the patient with food.

In some examples, the oral administration of the fixed dose comprises from 300 mg to 600 mg TU per day as twice a day with a divided dose (e.g., 150-300 mg TU administered as a divided dose).

In some examples, the oral administration of the fixed dose comprises 400-475 mg TU per day as twice a day with a divided dose (e.g., 200-238 mg TU administered as a divided dose).

In some examples, the oral administration of the fixed dose comprises 420-460 mg TU per day as twice a day with a divided dose (e.g., 210-230 mg TU administered as a divided dose).

In some examples, the oral administration of the fixed dose comprises 450 mg TU per day as twice a day with a divided dose (e.g., 225 mg TU administered twice a day).

In some examples, the oral administrating pharmaceutical composition comprising TU comprises one or more of lipophilic surfactants, hydrophilic surfactants, and combination thereof.

In some examples, the oral pharmaceutical composition comprising TU comprises at least one or more of a fatty acid, a monoglyceride, a diglyceride, a triglyceride, a hydrophilic surfactant, a solidifying agent, and a combination thereof.

The oral pharmaceutical compositions of dosage forms (e.g. capsule or tablet) comprising TU disclosed herein comprises at least one pharmaceutically acceptable carrier known in the art. Non-limited examples of pharmaceutical acceptable carriers include lipophilic additives, hydrophilic additives, other additives, and combinations thereof.

In one embodiment, the lipophilic additives include, but not limited to, lipidic solubilizers, lipophilic surfactants, and combinations thereof. The lipidic solubilizers can comprise at least about 30 wt % of the pharmaceutically acceptable carrier. Non-limiting examples of lipidic solubilizers can include triglycerides, tocopherol, tocopherol derivatives, fatty acids, fatty acid glycerides, or combinations thereof. The triglycerides can include hydrogenated soybean oil, hydrogenated vegetable oil, corn oil, olive oil, soybean oil, peanut oil, sesame oil, or combination thereof. In another embodiment, the fatty acids can include caprylic acid, capric acid, lauric acid, myristic acid, palmitic acid, stearic acid, richinoleic acid, arachidic acid, behenic acid, lignoceric acid, cerotic acid, myristoleic acid, palmitoleic acid, sapienic acid, oleic acid, elaidic acid, vaccenic acid, linoleic acid, γ-linoleic acid, linoeladic acid, arachidonic acid, erucic acid, or combinations thereof. In an additional embodiment, the fatty acid glycerides can be monoglycerides, diglycerides, or mixtures thereof. Non-limiting examples of fatty acid glycerides that can be used in the oral pharmaceutical composition include monoglycerides and/or diglycerides derived from sources such as maize oil, poppy seed oil, safflower oil, sunflower oil, borage seed oil, peppermint oil, coconut oil, palm kernel oil, castor oil, or mixtures thereof. In an embodiment, the glyceride derivatives described in the following surfactants may be used as lipidic solubilizers as well.

In an embodiment, a surfactant is considered as a lipophilic surfactant when it has an HLB value of 10 or less. It is important to note that some lipophilic surfactants may also function as the lipidic solubilizer component of the compositions and oral dosage forms. Various lipophilic surfactants can be used including, but not limited to mono-, di-glycerides of fatty acids like glyceryl monolinoleate (e.g. MAISINE 35-1), mono- and di glycerides of caprylic, capric acid (e.g. CAPMUL MCM), glyceryl monooleate, reaction mixtures of alcohols or polyalcohols with a variety of natural and/or hydrogenated oils such as PEG-5 hydrogenated castor oil, PEG-7 hydrogenated castor oil, PEG-9 hydrogenated castor oil, PEG-6 corn oil (e.g. LABRAFIL M 2125 CS), PEG-6 almond oil (e.g. LABRAFIL M 1966 CS), PEG-6 apricot kernel oil (e.g. LABRAFIL M 1944 CS), PEG-6 olive oil (e.g. LABRAFIL M 1980 CS), PEG-6 peanut oil (e.g. LABRAFIL M 1969 CS), PEG-6 hydrogenated palm kernel oil (e.g. LABRAFIL M 2130 BS), PEG-6 palm kernel oil (e.g. LABRAFIL M 2130 CS), PEG-6 triolein (e.g. LABRAFIL M 2735 CS), PEG-8 corn oil (e.g. LABRAFIL WL 2609 BS), PEG-20 corn glycerides (e.g. CROVOL M40), PEG-20 almond glycerides (e.g. CROVOL A40), lipophilic polyoxyethylene-polyoxypropylene block co-polymers (e.g. PLURONIC L92, L101, L121 etc.); propylene glycol fatty acid esters, such as propylene glycol monolaurate (e.g. Lauroglycol FCC), propylene glycol ricinoleate (e.g. Propymuls), propylene glycol monooleate (e.g. Myverol P-O6), propylene glycol dicaprylate/dicaprate (e.g. CAPTEX 200), and propylene glycol dioctanoate (e.g. CAPTEX 800), propylene glycol mono-caprylate (e.g. CAPRYOL 90); propylene glycol oleate (e.g. Lutrol OP2000); propylene glycol myristate; propylene glycol mono stearate; propylene glycol hydroxy stearate; propylene glycol ricinoleate; propylene glycol isostearate; propylene glycol mono-oleate; propylene glycol dicaprylate/dicaprate; propylene glycol dioctanoate; propylene glycol caprylate-caprate; propylene glycol dilaurate; propylene glycol distearate; propylene glycol dicaprylate; propylene glycol dicaprate; mixtures of propylene glycol esters and glycerol esters such as mixtures composed of the oleic acid esters of propylene glycol and glycerol (e.g. ARLACEL 186); sterol and sterol derivatives such as cholesterol, sitosterol, phytosterol, phytosterol fatty acid esters, PEG-5 soya sterol, PEG-10 soya sterol, PEG-20 soya sterol, and the like; glyceryl palmitostearate, glyceryl stearate, glyceryl distearate, glyceryl monostearate, or a combination thereof sorbitan fatty acid esters such as sorbitan monolaurate (e.g. Arlacel 20), sorbitan monopalmitate (e.g. Span-40), sorbitan monooleate (e.g. Span-80), sorbitan monostearate, and sorbitan tristearate, sorbitan monolaurate, sorbitan monopalmitate, sorbitan monooleate, sorbitan trioleate, sorbitan sesquioleate, sorbitan tristearate, sorbitan monoisostearate, sorbitan sesquistearate, and the like; fatty acids such as capric acid, caprylic acid, oleic acid, linoleic acid, myristic acid, menthol, menthol derivatives, lecithin, phosphatidyl choline, bile salts, cholesterol, sitosterol, phytosterol (e.g. GENEROL series from Henkel), PEG-5 soya sterol (e.g. Nikkol BPS-S, from Nikko), PEG-10 soya sterol (e.g. Nikkol BPS-10 from Nikko), PEG-20 soya sterol (e.g. Nikkol BPS-20 from Nikko), and the like, and mixtures thereof.

In one embodiment, hydrophilic additives are selected from the group comprising at least one of hydrophilic surfactants, celluloses, such as hydroxypropyl celluloses low molecular weight, low viscosity types (e.g. METHOCEL E5, E6, E10 E15, LV100 etc. grades) and hydroxypropyl celluloses having higher molecular weight, medium to high viscosity (e.g. METHOCEL K4M, K15M, K100M etc.), polyvinylpyrrolidones (e.g. Kollidon k17, K30 etc.), polyvinyl acetates, and combinations thereof.

In further embodiment, a surfactant comprises a hydrophilic surfactant when it has an HLB value of greater than 10. Non-limiting examples of hydrophilic surfactants include non-ionic surfactants, ionic surfactants and zwitterionic surfactants. Specifically the hydrophilic surfactants suitable for the current invention include, but not limited to alcohol-oil transesterification products; polyoxyethylene hydrogenated vegetable oils; polyoxyethylene vegetable oils; alkyl sulphate salts, dioctyl sulfosuccinate salts; polyethylene glycol fatty acids esters; polyethylene glycol fatty acids mono- and di-ester mixtures; polysorbates, polyethylene glycol derivatives of tocopherol and the like It should be noted that the combinations of two or more hydrophilic surfactants from the same or different classes are within the scope of this invention and are together can be referred to as the hydrophilic surfactant unless explicitly specified. In one embodiment, the hydrophilic additive can be a hydrophilic surfactant. Non-limiting examples of hydrophilic surfactants can include PEG-8 caprylic/capric glycerides, lauroyl macrogol-32 glyceride, stearoyl macrogol glyceride, PEG-40 hydrogenated castor oil, PEG-35 hydrogenated castor oil, sodium lauryl sulfate, sodium dioctyl sulfosuccinate, polyethylene glycol fatty acids mono- and di-ester mixtures, polysorbate 80, polysorbate 20, polyethylene glycol 1000 tocopherol succinate, phytosterols, phytosterol fatty acid esters, lanosterol PEG-24 cholesterol ether (e.g. Solulan C-24, Amerchol), PEG-30 soya sterol (e.g. Nikkol BPS-30, from Nikko), PEG-25 phyto sterol (e.g. Nikkol BPSH-25 from Nikko), PEG-30 cholestanol (e.g. Nikkol DHC, from Nikko), and mixtures thereof.

In another aspect, other additives described herein in the oral TU dosage forms (e.g. powder, granulate, particulate, bead, pellet, sprinkle, suspension, solution, tablet, or capsule) comprise at least one or more of binders, bufferants, diluents, disintegrants, flavors, colorants, taste-masking agents, resins, pH modifiers, lubricants, glidants, thickening agent, opacifying agent, humectants, desiccants, effervescing agents, plasticizing agents, antioxidants, solidifying agents, control release agents, and combinations thereof.

In one example, a solidifying agent is one kind of pharmaceutically acceptable additives that is in a solid physical state at room temperature. Typically, solidifying agents facilitate the solidification of the pharmaceutical compositions of the present invention at temperatures around room temperature. The compositions and capsule fill of the present invention, including those with solidifying agents, can be non-liquid at standard temperature and pressure. In an aspect, the composition and capsule fill can be semi-solid or solid at standard temperature and pressure. When present, the solidifying agent can comprise from about 0.1 wt % to about 20 wt % of the pharmaceutical composition or capsule dosage form. In one embodiment, the solidifying agent can melt at a temperature of about body temperature to about 75° C. Non-limiting examples of solidifying agents include polyethylene glycols; sorbitol; gelatin; stearic acid; cetyl alcohol; cetosterayl alcohol; paraffin wax; polyvinyl alcohol; glyceryl stearates; glyceryl distearate; glyceryl monostearate; glyceryl palmitostearate; glyceryl behenate; waxes; hydrogenated castor oil; hydrogenated vegetable oil; Vit E derivatives, bees wax, microcrystalline wax; sterols; phytosterols; phytosterols fatty acid esters, cholesterol and mixtures thereof. In one embodiment, the solidifying agent includes a polyethylene glycol (PEG) having molecular weight from about 1000 to about 20,000 and their mixtures. In another embodiment the solidifying agent includes one or more selected from the group consisting of polyethylene glycol; gelatin; stearic acid; polyvinyl alcohol; glyceryl stearates; glyceryl distearate; glyceryl monostearate; glyceryl palmitostearate; hydrogenated castor oil; hydrogenated vegetable oil and cholesterol. In an additional embodiment, the solidifying agent includes Vit E tocopherol PEG 1000 succinate or derivatives of d-a-TPGS. In one embodiment, the pharmaceutical composition can be a solid at about room temperature. In yet a further embodiment, a "not dissolved" crystalline testosterone ester can act as a solidifying agent.

The oral TU pharmaceutical compositions of the present invention can be formulated to take any dosage form commonly known in the pharmaceutical arts such as granules, tablet or capsule. In one embodiment, the oral pharmaceutical composition of the present invention can be formulated as oral dosage forms such as capsules or tablets. The capsule size can be any size known in the art and can vary depending on the desired dosage amount. For instance, in one embodiment, the capsule can be a hard gelatin capsule having a fill volume of about 0.25 mL to about 1.1 mL. Similarly, in another embodiment, the capsule can be a soft gelatin capsule having a fill volume of about 0.25 mL to about 1.5 mL.

In a specific embodiment, the compositions of the current invention can be formulated in the form of granules, powder mixtures or tablets. In a specific embodiment, the testosterone ester present in the dosage form can be present in the form of nanoparticles or amorphous particles, liquid, or mixtures thereof. In another specific embodiment, the testosterone ester present in these dosage form can be present in the form of crystalline, non-crystalline or amorphous particles or a mixtures thereof having an average particle size of about 2000 nm or less, 1500 nm or less, 1000 nm, 800 nm or less, 600 nm or less, 500 nm or less, 400 nm or less, 300 nm or less, 250 nm or less, 200 nm or less, 100 nm or less, 50 nm or less, or 25 nm or less; or the average particle size of said crystalline, non-crystalline or amorphous particles or a mixtures thereof is in the range 10 nm to 2000 nm, 10 nm to 1500 nm, 10 nm to 1000 nm, 10 nm to 800 nm, 10 nm to 750 nm; 10 nm to 600 nm, 10 nm to 500 nm, 10 nm to 400 nm, 10 nm to 300 nm, 10 nm to 250 nm, 10 nm to 200 nm, or 10 nm to 100 nm.

Exemplary Compositions—Oral TU Dosage Forms with Fixed Dose Regimen

Example A

| Ingredient Name | | | Dosage Form A1 | | Dosage Form A2 | |
|---|---|---|---|---|---|---|
| | | | % w/w | mg/unit | % w/w | mg/unit |
| Testosterone Undecanoate | | | 10-20 | 100-300 | 10-15 | 60-200 |
| Pharmaceutical acceptable carriers | Lipophilic additives* | e.g. Castor oil | — | — | 48-55 | 600-850 |
| | | e.g. Oleic acid | 60-90 | 900-1200 | — | — |
| | | e.g. Propylene glycol monolaurate | — | — | 30-40 | 400-600 |
| | Other additives** (e.g. antioxidant, solidifer,etc) | | 0-10 | 0-100 | 0-12 | 0-120 |
| Total | | | 100 | 1000-1600 | 100 | 1000-1650 |

*Lipophilic additives used in these compositions (e.g. castor oil, oleic acid, and propylene glycol monolaurate) can be replaced with other lipophilic additives or combinations described in the above contexts. This can be applied to all other examples.
**Other additives exemplified as antioxidant or solidifer in these compositions can be replaced with different other additives or combinations described in the above contexts. This can be applied to all other examples.

Example B

| Ingredient Name | | | Dosage Form B1 | | Dosage Form B2 | | Dosage Form B3 | |
|---|---|---|---|---|---|---|---|---|
| | | | % w/w | mg/unit | % w/w | mg/unit | % w/w | mg/unit |
| Testosterone Undecanoate | | | 10-18 | 100-180 | 20-32 | 150-300 | 18-25 | 130-300 |
| Pharmaceutical acceptable carriers | Lipophilic additives* | Mono/diglyceride 1 (e.g. Glyceryl monolinoleate) | 50-75 | 400-650 | — | — | — | — |
| | | Mono/diglyceride 2 (e.g. Glyceryl distearate) | — | — | 2-10 | 20-80 | — | — |
| | | Fatty acid1 (e.g. Oleic acid) | — | — | 45-70 | 250-650 | 45-65 | 350-800 |

-continued

| Ingredient Name | | Dosage Form B1 % w/w | Dosage Form B1 mg/unit | Dosage Form B2 % w/w | Dosage Form B2 mg/unit | Dosage Form B3 % w/w | Dosage Form B3 mg/unit |
|---|---|---|---|---|---|---|---|
| | Fatty acid2 (e.g. Stearic acid) | — | — | 2-8 | 15-60 | — | — |
| | Triglyceride1 (e.g. Borage oil) | — | — | — | — | 6-15 | 50-180 |
| | Triglyceride2 (e.g. Peppermint oil) | — | — | — | — | 2-6 | 10-50 |
| Hydrophilic additives** (e.g. Polyoxyl 40 hydrogenated castor oil) | | 2-18 | 60-200 | 2-8 | 15-60 | 10-18 | 80-250 |
| Other additives*** | Solidifiers (e.g. PEG) | 2-8 | 10-80 | — | — | — | — |
| | Antioxidant | 0-1 | 0-10 | 0-1 | 0-10 | 0-1 | 0-10 |
| Total | | 100 | 700-1250 | 100 | 600-1250 | 100 | 700-1350 |

*Lipophilic additives used in these compositions can be replaced with other lipophilic additives or combinations described in the above contexts. This can be applied to all other examples.
*Hydrophilic additives used in these compositions (e.g. polyoxyl 40 hydrogenated castor oil) can be replaced with other hydrophilic additives or combinations described in the above contexts. This can be applied to all other examples.
***Other additives exemplified as solidifier and antioxidant in these compositions can be replaced with different other additives or combinations described in the above contexts. This can be applied to all other examples.

Example C

| | | | Dosage Form C1 % w/w | Dosage Form C1 mg/unit | Dosage Form C2 % w/w | Dosage Form C2 mg/unit | Dosage Form C3 % w/w | Dosage Form C3 mg/unit |
|---|---|---|---|---|---|---|---|---|
| | Testosterone Undecanoate | | 10-15 | 140-200 | 10-15 | 140-200 | 10-15 | 140-200 |
| Pharmaceutical acceptable carriers | Lipophilic additives* | Triglyceride (e.g. Castor oil) | 22-28 | 300-450 | — | — | — | — |
| | | Fatty acid (Oleic acid) | — | — | 24-30 | 300-470 | 24-30 | 300-470 |
| | | Mono/diglyceride derivative (e.g. Propylene glycol monolaurate) | 15-18 | 200-300 | — | — | — | — |
| | | Mono/diglyceride (e.g. Glyceryl distearate) | — | — | — | — | 12-15 | 150-240 |
| | | Monoglyceride (e.g. Glyceryl monooleate) | — | — | 14-18 | 180-280 | 5-10 | 100-170 |
| | | Glyceride derivative (e.g. Oleoyl polyoxyl-6 glycerides) | 10-15 | 150-230 | 10-15 | 130-225 | 4-6 | 50-100 |
| | | Lipophilic surfactant (e.g. Lecithin) | 0.5-1.5 | 5-15 | 0.5-1.5 | 5-15 | 0.5-1.5 | 5-15 |
| | | Lipophilic surfactant (e.g. Phytosterol) | 1-3 | 25-40 | 1-3 | 25-40 | 1-3 | 25-40 |
| | Hydrophilic additives** | e.g. Polyoxyl 40 hydrogenated castor oil | 25-35 | 350-525 | 6-12 | 110-185 | 6-12 | 110-185 |
| | | e.g. Polysorbate 80 | — | — | 18-22 | 230-350 | 18-22 | 230-350 |
| | | e.g. D-α-tocopherol | — | — | 1-3 | 20-40 | 1-3 | 20-40 |
| | Other additives*** | Control release agent | 0.5-1.5 | 5-15 | 0.5-1.5 | 5-15 | 0.5-1.5 | 5-15 |
| | | Antioxidant | 0-0.3 | 0-1.0 | 0-0.3 | 0-1.0 | 0-0.3 | 0-10 |
| Total | | | 100 | 750-1300 | 100 | 750-1300 | 100 | 750-1300 |

*Lipophilic additives used in these compositions can be replaced with other lipophilic additives or combinations described in the above contexts. This can be applied to all other compositions.
*Hydrophilic additives used in these compositions can be replaced with other hydrophilic additives or combinations described in the above contexts. This can be applied to all other compositions.
***Other additives used in these compositions can be replaced with different other additives or combinations described in the above contexts. This can be applied to all other compositions.

It is understood that the above-described various types of compositions, dosage forms and/or modes of applications are only illustrative of preferred embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that variations including, but not limited to, variations in size, materials, shape, form, function and manner of operation, assembly and use may be made without departing from the principles and concepts set forth herein.

In the clinical study for this invention, the intensive PK sampling was performed by collecting blood samples withdrawn at 15 sampling time points through 24 hours after a morning dose of oral TU with the fixed 225 mg BID dose without dose adjustment. The single serum T concentration measured was at steady state (e.g., at least after 2 weeks after initiation of the oral TU dose). Table 1 shows the (normal) responder rate of continuing the oral TU therapy for patients assessed by monitoring single serum T concentrations at each time point after a morning dose of the fixed 225 mg BID oral TU administration at the first visit. The first visit was performed at 3 weeks after initiation of the oral TU therapy, of which T levels were at steady state.

Clinical Example for Exemplary Inventive Oral TU Composition Described Above

TABLE 1 proportion of subjects who are deemed to have effective therapy by monitoring serum T concentration measured at selected hours after morning dosing of the fixed 225 mg BID oral TU composition at the first visit.

| | Sample time point after a morning dose | | | | | | |
|---|---|---|---|---|---|---|---|
| | 3 Hour | 4 Hour | 5 Hour | 6 Hour | 7 Hour | 8 Hour | 9 Hour |
| Effective Responder* rate for continuation based on single serum T measurement | 46% | 50% | 66% | 64% | 68% | 71% | 72% |

*Effective Responder rate (proportion of plurality of patients in eugonadal (≥300 ng/dL and ≤1080 ng/dL) range)computed from observed patient T measurement from single point relative to effective responder rate observed with full T PK profile measurement based on T $C_{avg}$.

The results of the criteria applied after measuring single serum T concentration at the first visit after oral TU administration with the fixed 225 mg BID dose without dose titration demonstrated that single serum T measuring time window of 8 and 9 hours after a morning dose (T $C_{max}$ being reported to typically occur 6 hours or less after dose administration) is the most appropriate to determine the rate of the responder, and represents a patient continuation criteria of continuing the oral TU therapy: see responder rate at least 70% at 8 and 9 hours after a morning dose in Table 1. This is a novel finding compared to prior art TRT products which teach measurements at about 3-6 hours after dosing.

Concordance for continuation of the oral TU therapy based on monitoring single T concentration periodically (e.g., at least two visits) was evaluated with a combination of 8 and 9 hour time points at the first visit and subsequent visit. Table 2 summarizes the concordance for continuing the oral TU therapy after the second visit identified by single serum T concentrations measured at 8 and 9 hours after a morning dose of the fixed 225 mg BID oral TU composition. Multiple cases visited at the first visit and second visit. Possible test times after visits include: the first visit hour/second visit hour can be 8 hr/8 hr, 8 hr/9 hr, 9 hr/8 hr, and 9 hr/9 hr.

TABLE 2

Proportion of patients who are continued and in inappropriate discontinuation determined by measuring T concentration periodically, such as at least two visits

| | Sample time point at first visit and subsequent visit | | | | |
|---|---|---|---|---|---|
| | 8 hr/ 8 hr | 8 hr/ 9 hr | 9 hr/ 8 hr | 9 hr/ 9 hr | Mean |
| Effective Responder* rate for continuation based on single serum T measurement with at least 2 monitoring visits: Concordance for continuation | 83% | 86% | 84% | 83% | 84% |

Consistent with a TRT therapy goal of effective T restoration in at least 75% of group (normal) responders achieving effective T levels while on their steady state dose, as shown in Table 1 and 2, concordance of the continuation of the therapy after the second visit was improved from at least 71% at the first visit to at least 84% by monitoring single serum T concentration measured at 8 and 9 hours after a morning dose.

Moreover, the efficacy goal was achieved through novel oral TU fixed dose regimen, specifically, a dose of 225 mg BID fixed dose without any dose adjustment.

It is understood that the above-described various types of compositions, dosage forms and/or modes of applications are only illustrative of preferred embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that variations including, but not limited to, variations in size, materials, shape, form, function and manner of operation, assembly and use may be made without departing from the principles and concepts set forth herein.

What is claimed is:

1. A Testosterone Undecanoate (TU) pharmaceutical composition for restoring an effective amount of T concentration in a hypogonadal male subject in response to a fixed dose oral administration therapy regimen thereof, wherein said composition includes a continuation criteria comprising a single serum T concentration level measured at a steady state 3 to 4 weeks after initiation of said regimen and 8 to 9 hours after administering a morning dose of said regimen, wherein if said single serum T measured concentration level is within a range of 300 ng/dL to 1080 ng/dL, said regimen is continued, and wherein if said single serum T concentration level is not within a range of 300 ng/dL to 1080 ng/dL, said regimen is discontinued.

2. The composition of claim 1, wherein said regimen comprises a daily administration of 450 mg of TU.

3. The composition of claim 1, wherein said regimen comprises a twice daily administration of 225 mg of TU.

4. The composition of claim 3, wherein said 225 mg of TU comprises two capsules, and wherein each capsule comprises 112.5 mg of TU.

5. The composition of claim 1, wherein said regimen comprises administration of said composition with food.

6. The composition of claim 1, wherein said subject has a testosterone concentration below at least one of 300 ng/dL, 250 ng/dL, 200 ng/dL, 150 ng/dL, and 100 ng/dL, and wherein in response to said regimen, a T $C_{avg}$ of said subject is increased.

7. The composition of claim 6, wherein said increase of said T $C_{avg}$ comprises a minimum increase of at least one of 30 ng/dL, 50 ng/dL, 75 ng/dL, 100 ng/dL, 150 ng/dL, 200 ng/dL, 300 ng/dL, 400 ng/dL, 500 ng/dL, 600 ng/dL, 700 ng/dL, 800 ng/dL and greater than 800 ng/dL.

8. The composition of claim 1, wherein said composition has a responder rate of at least 75%.

9. The composition of claim 1, wherein said single serum T concentration level measured at a steady state comprises a periodic single serum T concentration level measured at a steady state.

10. A Testosterone Undecanoate (TU) pharmaceutical composition for restoring an effective amount of T concentration in a hypogonadal male subject in response to a fixed dose oral administration therapy regimen thereof, wherein said composition includes a continuation criteria comprising the monitoring of a single serum T concentration level measured at a steady state 8 to 9 hours after a morning dose 3 to 4 weeks after initiating said regimen and periodically thereafter, wherein if said measured serum T concentration level is within the range of 300 ng/dL to 1080 ng/dL, said regiment is continued, and wherein if said measured serum T concentration level is less than 300 ng/dL, said regiment is discontinued, and wherein if said measured serum T concentration level is greater than 1080 ng/dL, said regiment is discontinued.

11. The composition of claim 10, wherein said regimen comprises a daily administration of 450 mg of TU.

12. The composition of claim 11, wherein said regimen comprises a twice daily administration of 225 mg of TU.

13. The composition of claim 12, wherein said 225 mg of TU comprises two capsules, and wherein each capsule comprises 112.5 mg of TU.

14. The composition of claim 10, wherein said regimen comprises administration of said composition with food.

15. The composition of claim 10, wherein said subject has a testosterone concentration below at least one of 300 ng/dL, 250 ng/dL, 200 ng/dL, 150 ng/dL, and 100 ng/dL, and wherein in response to said regimen, a T $C_{avg}$ of said subject is increased.

16. The composition of claim 15, wherein said increase of said T $C_{avg}$ comprises a minimum increase of at least one of 30 ng/dL, 50 ng/dL, 75 ng/dL, 100 ng/dL, 150 ng/dL, 200 ng/dL, 300 ng/dL, 400 ng/dL, 500 ng/dL, 600 ng/dL, 700 ng/dL, 800 ng/dL and greater than 800 ng/dL.

17. The composition of claim 10, wherein said composition has a responder rate of at least 75%.

18. A method of continuing or discontinuing a fixed dose oral administration regimen of a TU pharmaceutical composition comprising:
  initiating said regimen to a hypogonadal male subject having a testosterone concentration below 300 ng/dL;
  measuring a steady state single serum T concentration level 8 to 9 hours after administration of a morning dose of said regimen three to four weeks after initiation of said regimen; and
  continuing said regimen if said measurement is within a range of 300 ng/dL to 1,080 ng/dL and discontinuing said regimen if said measurement is not within a range of 300 ng/dL to 1,080 ng/dL.

19. The method of claim 18, wherein said regimen comprises a daily administration of 450 mg of TU.

20. The method of claim 19, wherein said regimen comprises a twice daily administration of 225 mg of TU.

21. The method of claim 20, wherein said 225 mg of TU comprises two capsules, and wherein each capsule comprises 112.5 mg of TU.

22. The method of claim 18, wherein said regimen comprises an administration of said composition with food.

23. The method of claim 18, wherein in response to said regimen, a T $C_{avg}$ of said subject is increased.

24. The method of claim 23, wherein said increase of said T $C_{avg}$ comprises a minimum increase of at least one of 30 ng/dL, 50 ng/dL, 75 ng/dL, 100 ng/dL, 150 ng/dL, 200 ng/dL, 300 ng/dL, 400 ng/dL, 500 ng/dL, 600 ng/dL, 700 ng/dL, 800 ng/dL and greater than 800 ng/dL.

25. The method of claim 18, wherein said method has a responder rate of at least 75%.

26. The method of claim 18, wherein said measuring step comprises a periodic measuring step.

27. A method of continuing or discontinuing a fixed dose oral administration regimen of a TU pharmaceutical composition comprising:
  initiating said regimen to a hypogonadal male subject having a testosterone concentration below 300 ng/dL;
  measuring a steady state single serum T concentration level 8 to 9 hours after administration of a morning dose of said regimen three to four weeks after initiation of said regimen; and
  continuing said regimen if said measurement is within a range of 300 ng/dL to 1,080 ng/dL.

28. The method of claim 27, wherein said regimen comprises a daily administration of 450 mg of TU.

29. The method of claim 28, wherein said regimen comprises a twice daily administration of 225 mg of TU.

30. The method of claim 29, wherein said 225 mg of TU comprises two capsules, and wherein each capsule comprises 112.5 mg of TU.

31. The method of claim 27, wherein said regimen comprises an administration of said composition with food.

32. The method of claim 27, wherein in response to said regimen, a T $C_{avg}$ of said subject is increased.

33. The method of claim 32, wherein said increase of said T $C_{avg}$ comprises a minimum increase of at least one of 30 ng/dL, 50 ng/dL, 75 ng/dL, 100 ng/dL, 150 ng/dL, 200 ng/dL, 300 ng/dL, 400 ng/dL, 500 ng/dL, 600 ng/dL, 700 ng/dL, 800 ng/dL and greater than 800 ng/dL.

34. The method of claim 27, wherein said method has a responder rate of at least 75%.

35. The method of claim 27, wherein said measuring step comprises a periodic measuring step.

36. The method of claim 27, wherein said method includes the step of discontinuing said regimen if said measurement is not within a range of 300 ng/dL to 1,080 ng/dL.

* * * * *